US008649510B2

(12) United States Patent
Knepper et al.

(10) Patent No.: US 8,649,510 B2

(45) Date of Patent: Feb. 11, 2014

(54) DEVICE HAVING CODED OUTPUT OF OPERATIONAL DATA

(75) Inventors: Michael B. Knepper, Friedens, PA (US); Stephen F. Krepelka, Berlin, PA (US)

(73) Assignee: DeVilbiss Healthcare, LLC, Somerset, PA (US)

( * ) Notice: Subject to any disclaimer, the term of this patent is extended or adjusted under 35 U.S.C. 154(b) by 565 days.

(21) Appl. No.: 12/543,631

(22) Filed: Aug. 19, 2009

(65) Prior Publication Data

US 2010/0199102 A1 Aug. 5, 2010

Related U.S. Application Data

(60) Provisional application No. 61/148,666, filed on Jan. 30, 2009.

(51) Int. Cl.

*G06F 21/00* (2013.01)

*H04L 9/00* (2006.01)

(52) U.S. Cl.

USPC .......................................... 380/28; 128/204.26

(58) Field of Classification Search

USPC .......................................................... 713/189

See application file for complete search history.

(56) References Cited

U.S. PATENT DOCUMENTS

| | | | | |
|---|---|---|---|---|
| 4,967,756 | A * | 11/1990 | Hewitt | 600/493 |
| 6,456,875 | B1 | 9/2002 | Wilkinson et al. | |
| 7,285,090 | B2 * | 10/2007 | Stivoric et al. | 600/300 |
| 2003/0135127 | A1 | 7/2003 | Sackner et al. | |
| 2003/0236450 | A1 | 12/2003 | Kocinski | |

FOREIGN PATENT DOCUMENTS

| | | |
|---|---|---|
| JP | 2005-242635 | 8/2005 |
| WO | 02/47747 A1 | 6/2002 |
| WO | 2006/133495 A1 | 12/2006 |

* cited by examiner

*Primary Examiner* — Gilberto Barron, Jr.

*Assistant Examiner* — Simon Kanaan

(74) *Attorney, Agent, or Firm* — Fox Rothschild LLP; Dennis M. Carleton

(57) ABSTRACT

A device for confirming compliance with usage of a breathing gas delivery system that includes at least one sensor for monitoring operating data disposed within the breathing gas delivery system and a device for encoding the monitored operating data and displaying the encoded operating data for reporting to another location.

21 Claims, 7 Drawing Sheets

SmartCode Enhanced Samples

| S | m | a | r | t | C | o | d | e | | | 1 | - | D | a | y |
|---|---|---|---|---|---|---|---|---|---|---|---|---|---|---|---|
| z | x | 5 | - | F | A | 1 | - | I | P | O | T | | | | |

| S | m | a | r | t | C | o | d | e | | | 7 | - | D | a | y |
|---|---|---|---|---|---|---|---|---|---|---|---|---|---|---|---|
| z | y | 9 | - | U | F | B | - | R | 6 | S | 3 | | | | |

| S | m | a | r | t | C | o | d | e | | 3 | 0 | - | D | a | y |
|---|---|---|---|---|---|---|---|---|---|---|---|---|---|---|---|
| u | 8 | Y | - | R | 9 | L | - | E | T | A | S | | | | |

FIG. 5

Enhanced SmartCode Input Form

Provider Info
Sleep For You
123 Second Street
Hackensack, NJ 00123

Patient Info
Dan Schmidt
333 Apple St.
Smithton, NJ

Physician Info
Dr. Sleepwell
Sleepwell Associates

Device Info
Auto Adjust
15/5 cmH20

| Code ID | Smart Code | Validation |
|---|---|---|
| 1 Day | | |
| 7 Day | | |
| 30 Day | | |
| 90 Day | | |
| Cumulative | | |

Generate Report

Provider clicks "Generator" button

FIG. 6

Enhanced SmartCode Report Output

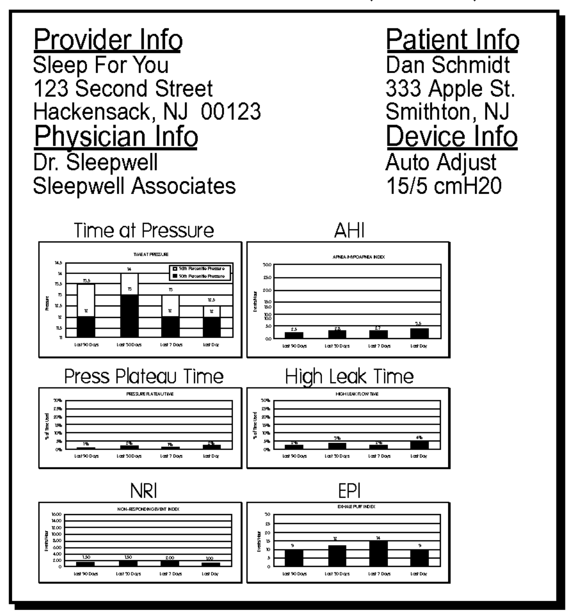

Report can be printed or saved

FIG. 7

DEVICE HAVING CODED OUTPUT OF OPERATIONAL DATA

RELATED APPLICATIONS

This application claims the benefit of U.S. Provisional Application No. 61/148,666, filed Jan. 30, 2009, the disclosure of which is incorporated herein by reference.

FIELD OF THE INVENTION

This invention is related to the field of breathing gas delivery machines, such as continuous positive airway pressure (CPAP) machines of the type typically used to treat patients suffering from breathing disorders, such as hypopnea or apnea, and, in particular, is related to such machines that are capable of collecting data regarding the patient's use of the machines and the various operational parameters of the machine.

BACKGROUND OF THE INVENTION

Many sleep related respiratory conditions, for example, snoring, are caused by a blockage or partial blockage of the respiratory tract. As the blockage increases, hypopnea, or a reduction of air flow to the lungs, occurs. Apnea, or a temporary cessation of breathing, can occur when the airway becomes totally blocked. A person suffering from sleep apnea may have difficulty functioning during the day because of insufficient sleep caused by the apnea events. In severe cases, the person also can suffer from problems caused by reduced blood oxygen levels.

One form of treatment for severe snoring, hypopnea and sleep apnea involves the application of a breathing gas delivery system to the person's respiratory tract while sleeping. Sufficiently high positive airway pressure (PAP) is applied to the person's airway to prevent its collapse or blockage. The applied positive, pressure supplied by a breathing gas delivery system, is usually within a range of 3 to 20 cm $H_2O$.

Referring now to FIG. 1, there is shown a typical known breathing gas delivery system 10. The breathing gas delivery system 10 comprises a control unit 12, a flexible tube 14, and a suitable device for injecting air into the user's nasal passages, such as a face mask 16. The face mask 16 is typically designed to cover the user's nose and/or mouth and forms an air-tight seal with the face of the user 18. The mask 16 preferably includes adjustable straps 20 and 22 for adjusting the tightness of the mask on the face of the user 18.

The control unit 12 includes a regulated blower (not shown) that supplies a flow of air to the face mask 16 via the flexible tube 14. The control unit 12 includes a first switch 24 for turning on the breathing gas delivery system 10. Typically, when the breathing gas delivery system 10 is initially turned on, the system supplies breathing gas at a comfortable lower pressure to the person while he falls asleep. The breathing gas delivery system then gradually increases the pressure of the supplied breathing gas to a prescribed therapeutic level. Accordingly, the control unit 12 may include a second switch 26 for controlling the time period for increasing the supplied breathing gas pressure.

The breathing gas delivery system 10 is calibrated following testing that is usually conducted at a sleep clinic. With proper use, the breathing gas delivery system 10 will overcome hypopnea and sleep apnea and allow the user to receive adequate sleep.

Some users, however, may experience difficulty or discomfort using their breathing gas delivery system and may terminate its use during the night, or even stop using the system entirely. Physicians, both for reasons of providing adequate treatment for the patients, and also for reason of medical reimbursements, need to verify that the systems are being used as prescribed and are providing effective relief for the patients. Accordingly, there is a need to assure that the patients are using the system in compliance with the prescribed instructions that are issued with the breathing gas delivery system.

To monitor compliance and to gauge the effectiveness of the prescribed treatment, many such systems are capable of storing usage information, including, for example, information regarding the number of events which are detected during each sleep session and the pressures being used. Such information can be stored in the system over multiple sleep sessions, extending, in some cases, for many weeks. To read the information, a read-out of some sort may be provided that can be read to the doctor's office over the phone. However, this method of information exchange is susceptible to falsification, for example, by a patient who is embarrassed that the machine is not being used in the prescribed manner, or by a doctor's office to ensure reimbursement when such reimbursement may not otherwise be appropriate. To avoid such situations, it would be desirable to provide a method of exchanging such information that is resistant to tampering, but which may still be transferred person-to-person via a telephone.

SUMMARY OF THE INVENTION

This invention provides a system and method for confirming compliance with prescribed instructions for use of a breathing gas delivery system in a manner that discourages falsification of the data. The system monitors and stores usage data and includes a component for encoding the stored data, as well as a display for displaying the encoded data, such that the actual operating parameters and data are obfuscated to the sender and receiver of the data.

The present invention also contemplates a system and method for confirming compliance with prescribed usage instructions which includes a software-based facility for the verification and decoding of encoded data read from the system's display. The method includes providing a software facility that can be implemented either as an internet-accessible utility or as a locally running application that allows the entry of encoded data from the system's display interface and the generation of reports based on a decoding of the encoded data.

Various objects and advantages of this invention will become apparent to those skilled in the art from the following detailed description of the preferred embodiment, when read in light of the accompanying drawings.

BRIEF DESCRIPTION OF THE DRAWINGS

FIG. 5 shows typical samples of encoded data generated from the data collected by the device of the present invention.

FIG. 6 illustrates one possible embodiment of an input screen for entering encoded data collected from the device of the present invention.

FIG. 7 illustrates a typical report screen generated by the decoding and report generation components of the present invention.

DETAILED DESCRIPTION OF THE INVENTION

The present invention provides a system and method for reporting operating data for a breathing gas delivery system, such as a bi-level breathing gas machine or a CPAP machine, that will show compliance with prescribed user operating instructions in a manner that discourages tampering with the data by the patient or by the person receiving the data from the patient.

The invention consists of a breathing gas delivery system that monitors and stores selected system parameters and collected operating data. The data is accumulated over time and can be retrieved via a display on the device. Before displaying the data, the data is encoded and the encoded data is thereafter displayed. The device user then communicates the encoded data to another party, for example, a sleep clinic or physician (hereinafter referred to as a "provider"). The encoded data contains the system parameters and operating data to inform the provider as to whether or not the breathing device user is complying with the prescribed usage instructions. The encoded data will appear as readable ASCII characters which can easily be read from the display by the user and communicated to the provider. The encoding of the data simplifies the data reporting process and is not subject to potential manipulation by the device user because the user is unaware of the coding scheme which is being used to encode the data. Thus, the user is unaware of what data is being collected by the provider.

Figure 1:
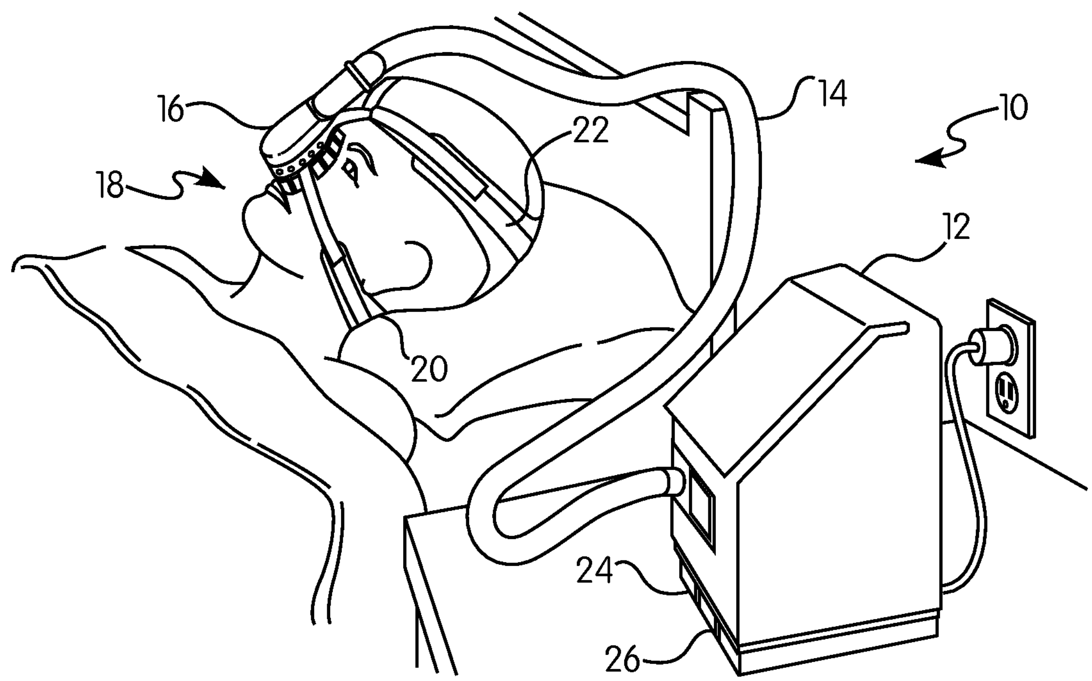
FIG. 1 illustrates a typical known breathing gas delivery system.
Figure 2:
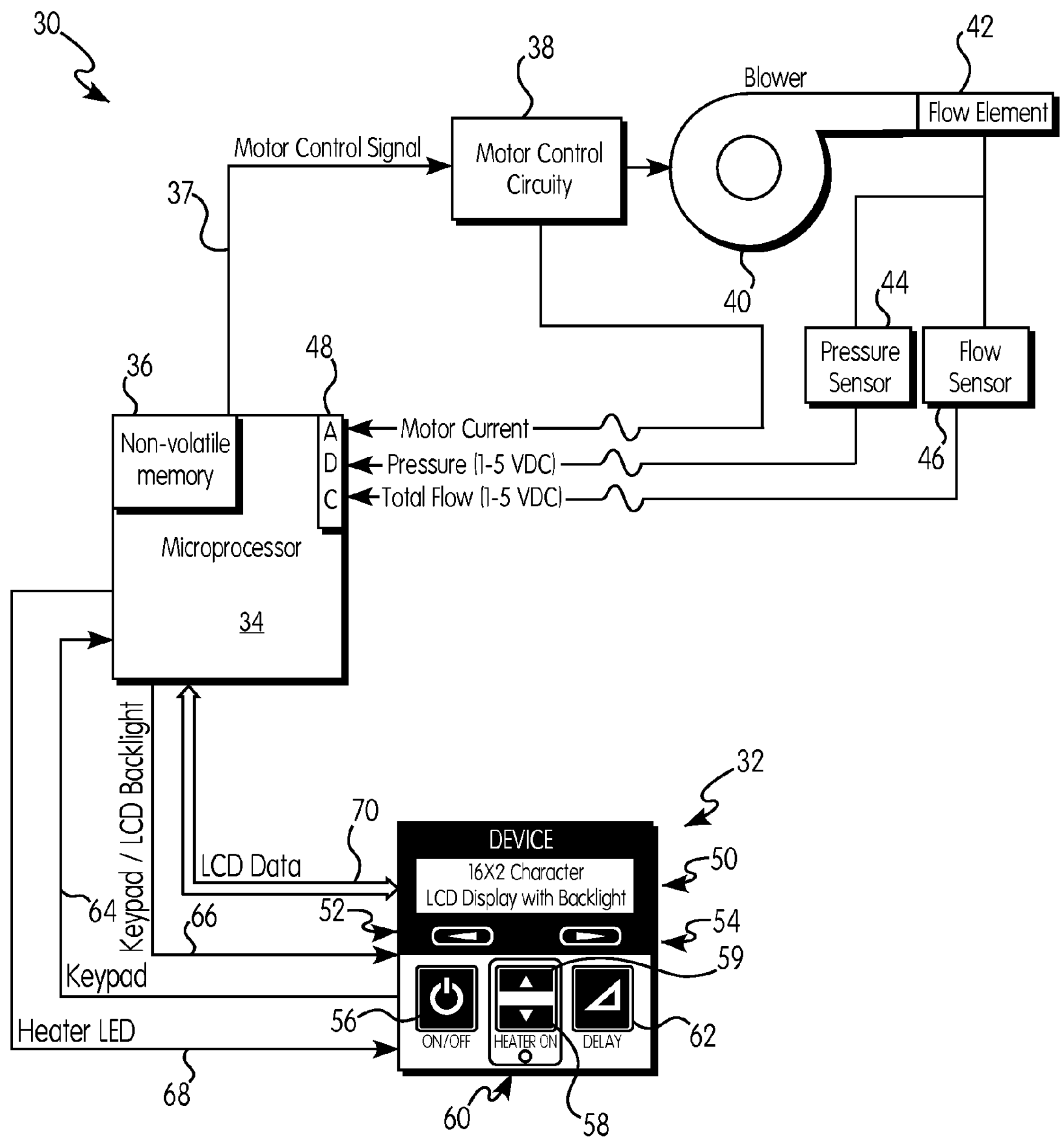
FIG. 2 is a block diagram of the components of one possible embodiment of the control unit of the present invention.

FIG. 2 is a block diagram of the device of the present invention. Similar to the prior art breathing gas delivery system 12 shown in FIG. 1, the device is connected through a flexible tube (not shown) to a face mask (also not shown) that is adapted to be strapped to the face of a user. The device includes a user interface panel 32 that is mounted on the outer surface of the unit. User interface panel 32 includes alphanumeric display 50 and one or more control buttons 52, 54, 56, 58, 59 and 62. Also included may be one or more LED-type indicators 60. It should be realized that the actual configuration and the number and types of buttons contained on user interface panel 32 can vary from embodiment to embodiment, and may be dependent upon the operating features of a particular unit.

Figure 3:
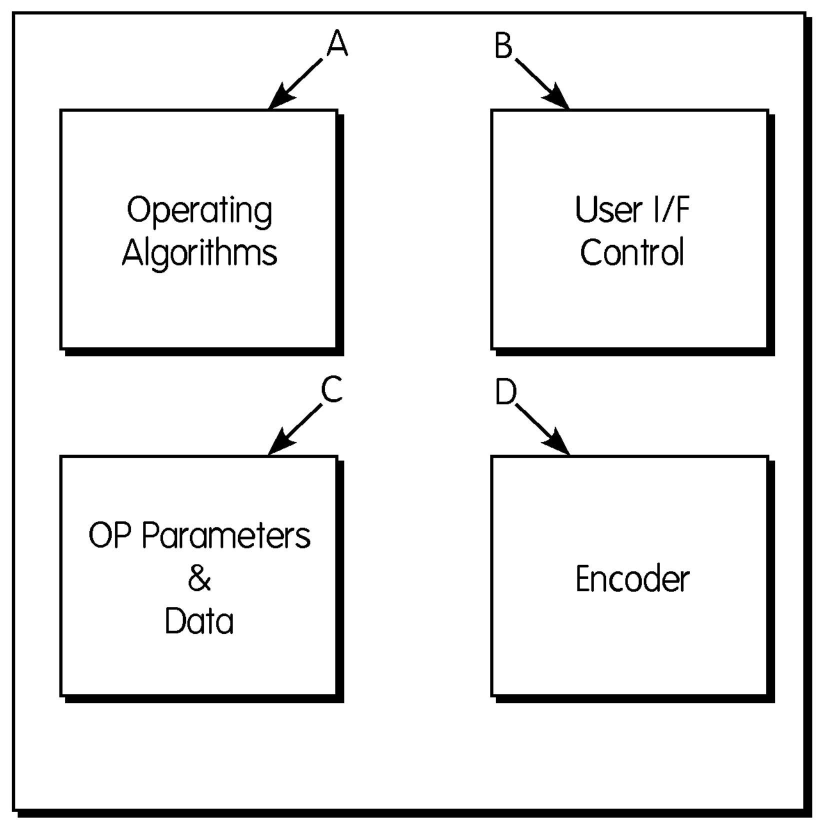
FIG. 3 is a block diagram of one possible arrangement of items stored in the non-volatile memory of the device of the present invention.

Microprocessor 34 and non-volatile memory 36 control the functioning of the unit. Non-volatile memory 36 may be broken down as shown in FIG. 3 and includes operating algorithms **36*a*, user interface control 36*b*, encoder 36*c* and storage for operating parameters and collected data 36*d*. As will be realized by one of skill in the art, many configurations for the structure of non-volatile memory are possible. In one possible alternative embodiment, the unit may be provided with a separate microprocessor or Application Specific Integrated Circuit (ASIC) dedicated to the collection, storage and manipulation of the system parameters and selected operating data (not shown). Such dedicated components may use either the original memory hardware 36** or a separate dedicated memory for storing the data. Memory for the storage of operating algorithms and collected data can include any type of memory well known in the art, including non-volatile RAM, flash media and hard drives, any of which may be internal or external to the device.

Operating algorithms **36*a* control the varying of the pressure in flow element 42 based on a monitoring of the user's breathing patterns, as sensed by pressure sensor 44 and flow sensor 46**. The actual algorithms will vary from unit to unit and are, in some instances, separately patented or guarded as trade secrets.

Interface control **36*b* accepts input from user interface panel 32 and controls the display 50. Display 50 is used to display all data input to and output from the unit, including the encoded operating parameters and collected data. Encoder 35*c* contains the algorithm for encoding the operating parameters, while data storage 36*d*** stores the unencoded operating parameters and collected data.

Microprocessor 34 may also include a clock that provides timing data that is stored in the non-volatile memory **36*d*. The timing data is utilized in calculating selected operating performance data from the raw data obtained from the motor current, gas pressure sensor 44 and flow rate sensor 46 in addition to tracking usage of the breathing gas delivery system. The unit may also contain algorithms in 36*a*** for determining when a sleep session begins and ends.

Microprocessor 34 is electrically connected to motor control circuitry 38 that, in turn, is electrically connected to blower 40. Blower 40 provides pressurized breathing gas to the flexible tube (not shown) via flow element 42. Motor control circuitry 38 is operative to control the speed of blower 40, and, thus, the pressure and flow rate of the air forced into flow element 42.

Pressure sensor 44 and flow sensor 46 are provided to monitor the pressure and flow rate, respectively, of the air passing through flow element 42. Feedback voltages representing the blower motor current, the air pressure and the air flow rate are supplied by motor control circuitry 38, pressure sensor 44 and flow sensor 46, respectively, to an analog to digital converter 48 that converts the data to a digital format for use by operating algorithms **36*a* and for storage in data storage memory 36*d*. As shown in FIG. 2, analog to digital converter 48 is included in the microprocessor 32, however, the invention also may be practiced with an analog to digital converter that is separate from the microprocessor 32** (not shown).

As also shown in FIG. 2, microprocessor 34 is connected to user interface panel 32. In the preferred embodiment, user interface panel 32 includes a backlit display 50, preferably a liquid crystal display (LCD) that displays selected encoded system operating parameters and data related to the use of the breathing gas delivery system. While a 16×2 display having two rows of 16 alpha-numeric characters is shown in FIG. 3, it will be appreciated that the invention also may be practiced utilizing displays having a different size and of a different type.

In one embodiment of the invention, reverse and forward pushbuttons labeled 52 and 54, respectively, are mounted immediately below LCD display 50. Reverse and forward pushbuttons 52 and 54 carry arrow indicia and are utilized to sequence display 50 through a series of displays showing various settings or menus for controlling the machine, one of which is the display of the encoded operating data. Forward pushbutton 54 is operative to advance the display while reverse pushbutton 52 is operative to move the display in the opposite direction. Up and down buttons 59 and 58 respectively are operative to make selections within settings or menus selected using left and right buttons 52 and 54. When the display is advanced using buttons 52 and/or 54 to the display which shows the encoded operating data, up and down buttons 59 and 58 may be used to display the different strings of ASCII characters representing the various groups of encoded operating data. As an example, the first string displayed may represent the operating data for the current session, and pressing the up or down arrow key may advance the display to a different string representing the 7, 30 or 90 days operating data.

Pushbutton 56, on the left of the operating panel 32, turns the control unit 30, and thereby the breathing gas delivery system, on or off. A light emitting diode or other type of indicator 60 positioned below buttons 58 and 59 indicates that the heater is on when illuminated. Pushbutton 62, on the right of the operating panel 32, may be used to activate a system delay which causes the initial flow of air to be supplied at a reduced pressure. The air pressure is then gradually increased to the operating pressure over a period of time.

Arrowheads in FIG. 2 indicate the direction of data flow between the operating panel 32 and the microprocessor 34. Thus, signals generated by operation of the described buttons are communicated from user interface panel 32 to microprocessor 34 via line 64. The backlight of the panel and display 50 is controlled by line 66. Heater LED 60 is controlled by line 68 and the selected system operating parameter data is transferred between the microprocessor 34 and display 50 over line 70.

It will be appreciated that FIG. 2 is a schematic drawing and that while one line may be shown, a plurality of electrical connections may be utilized to transfer data between the various components illustrated in the figure.

The present invention utilizes an ASCII encoding scheme to display the stored operating parameters and data to the system user. Microprocessor 34 includes an algorithm, stored in non-volatile memory 36*c*, for converting the operating parameters and data stored in the non-volatile memory 36*d* into the encoded data strings consisting of ASCII characters which may be read from display 50 and communicated by voice from the patient to the provider. The encoded data strings include the following features:

Code identity—Each encoded data string contains within itself an identification of the code type and therapy device type. The code identity is verified in a report generator, described below, to ensure it is the code that was requested from the user, or patient, to help identify if transcription errors have occurred in the reading or recording of the code.

Check byte(s)—The encoded data string contains one or more characters used to help identify if there is an error in the transcription of the data. During preparation of the encoded data string, a cyclic redundancy check (CRC) operation is performed on the encoded data string and a comparison to one or more check characters within the encoded data string is completed when the code is received.

Device identification (Serial Number)—At least one of the encoded data strings also contains a check character based on a device-specific identifier, such as the serial number of the device. The identifier is run through a CRC calculation and the result is converted to a character and included with one of the encoded data strings. Alternatively the whole identifier or a portion thereof may be encoded and included in it's own encoded string or as a portion of another encoded data string.

Compression—Operating parameters and data are compressed by using the full range of possible values for containing data, and adjusting the resolution of each reported parameter. Therefore, for example, a parameter such as average pressure has a resolution of 0.5 cm $H_2O$ but the resolution of AH1 is 0.25, although it should be realized that any resolution may be used Encoding/Obfuscation—The operating parameters and data are obfuscated in the encoded data string by encoding it in a format which is difficult to interpret by the typical patient. This allows the patient to report information from the device by reading the codes without knowing the interpretation of information contained in the code.

Live—Daily summary data is recorded in the non-volatile memory in the device, including the data for the most immediate day being used.

(a) "On-the-fly" generation of the codes—The encoded data strings are preferably generated by reading the recorded data and calculating averages for 7 day, 30 day, 90 day and cumulative usage, although any time periods for averaging the data may be used (b) Current session reported while in process—The most immediate day is also reported, and is accurate even while the device is being used and the current "session" is still in process.

The present invention further contemplates an application with a provider interface and supporting software for the decoding of the encoded data strings and the generation of reports from the operating parameters and data. The application used by the system is contemplated as being hosted on a web server and is accessible via a uniform resource locator (URL) using a standard web browser. Alternately, the application may be based upon a main frame or personal computer local to the provider.

Figure 4:
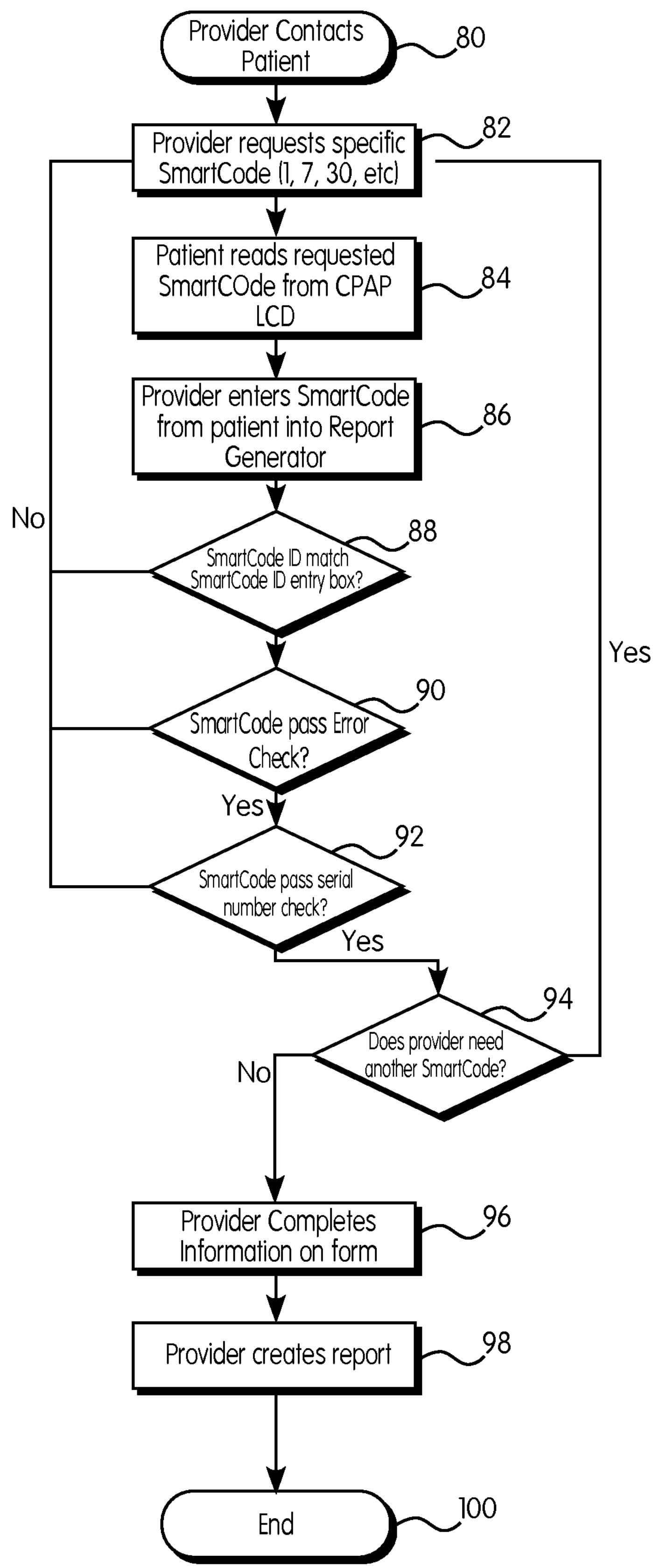
FIG. 4 is a flow chart illustrating the process for retrieving encoded data from the device of the present invention.

A flow chart illustrating the provider's interaction with the application is shown in FIG. 4. The application is entered through block 80 with the provider, such as a sleep clinic or physician, contacting the user of the breathing gas delivery system. The contact with the user may be, for instance, over the phone, but may also be accomplished in other ways, such as via a web site, email, SMS message or any other method convenient for communicating the encoded data strings from the user to the provider. It is not contemplated that the user will generally have access to the application that decodes the encoded data strings or that generates the reports.

In block 82, the provider requests a specific code and the user repeatedly presses up arrow buttons 59 on user interface panel 32 until the desired code is displayed on display 50. Should the user pass the desired code, down button 58 may be used to reverse the direction of the display and to access an encoded data string that occurs earlier in the display sequence. Pressing the up or down arrow buttons also activates the calculation of the selected encoded data strings by encoder 36*c*, which also occurs in block 82. The invention contemplates five reporting encoded data strings, namely:

a last day code representing the most recent operating parameters and data;

a 7 day code representing an average of most recent seven days of operating parameters and data;

a 30 day code representing an average of most recent 30 days of operating parameters and data;

a 90 day code representing an average of most recent 90 days of operating parameters and data; and a cumulative usage code representing an average of all the days of operating parameters and data obtained since the memory was reset to zero.

It will be appreciated that the invention may also be practiced to provide more or less encoded data strings than are listed above and that the encoded data strings may be programmed for other time periods than those shown above, and may contain different operating parameters and data. Additionally, the invention may be used with other types of devices, for example, blood pressure monitors, blood sugar level monitors, etc., and other non-medical devices.

Three typical displays are illustrated in FIG. 5 and show the encoded data strings for one day, seven days and 30 days respectively. In the preferred embodiment, codes may be display representing operating parameters and data for the last 1, 7, 30 and 90 days, as well as a code representing the cumulative averages for each operating parameters and data.

It is noted that the first line of the display preferably provides an un-encoded identification of the data (i.e., "1-day") as shown in FIG. 5., while the second line of the display is an encoded ASCII string that actually represents the operating parameters and data to be presented. While ten characters are shown in the second line of the codes shown in FIG. 5, the code may include more or less characters. Additionally, a larger display may be used that can display more than one code at a time.

As described above, data is obfuscated by using a set of conversion tables, each of which has as an index the set or a subset of the characters comprising readable ASCII characters. Certain letters and numbers may be omitted to avoid confusion—for instance, "S" and "5" may easily be confused when read on an electronic display, as can "I" and "1", "O" and "0" and "V" and "U". As a result, the total number of characters which may be displayed may be less than the total number of ASCII characters. Preferably, characters will be grouped in groups of 3-5 characters separated by a dash or other separator character to make the display easy to read and communicate.

In one embodiment of the invention, the encoded ASCII string may be derived as follows. The characters displayed are an index to a table of potential values for various parameters or particular types of operational data. These values in the table will have a range and will be scaled to a resolution that is dependent on the type of data being represented, with each ASCII character representing a specific value or a range of value within the overall possible range of values for the particular parameter.

The particular parameter for which the character represents a value is dependent upon the position within the encoded ASCII string displayed on the unit. As an example, an encoded ASCII string representing the activity for the current day may include, in a preferred embodiment, characters representing the following information:

decode information & the low use threshold;
the length of the most recent day;
the 90$^{th}$ percentile pressure;
the pressure plateau time percentage;
the % of therapy time that a leak is detected;
the apnea/hypopnea events per hour index;
the non-responding events per hour index;
the exhalation puff index;
miscellaneous info (may be a bit field);
an 8-bit CRC based on the unit's serial number;
an 8-bit CRC based on the encoded alphanumeric string Thus, the third character in the string may be an index to a table of pressure readings, expressed in a pre-defined range as pre-defined steps. Preferably, the characters, when used as indices to the tables of potential values for each parameter will not be arranged in order, but will be arranged in a random order to provide greater obfuscation of the values being encoded. Each character is also assigned a numerical value which may be useful if a particular character position with the string represents a bit field.

Alternatively, the data may be encrypted (not shown) using any one of a number of well know data encryption algorithms.

It will be appreciated that use of the unencoded title strings shown on the first line of the displays in FIG. 5 are meant to be illustrative and that the invention also may be practiced with other displays, representing, for example, other ranges of data. Naturally, other implementations, including for machines other than CPAP machines, will have different parameters represented.

Figure 8:
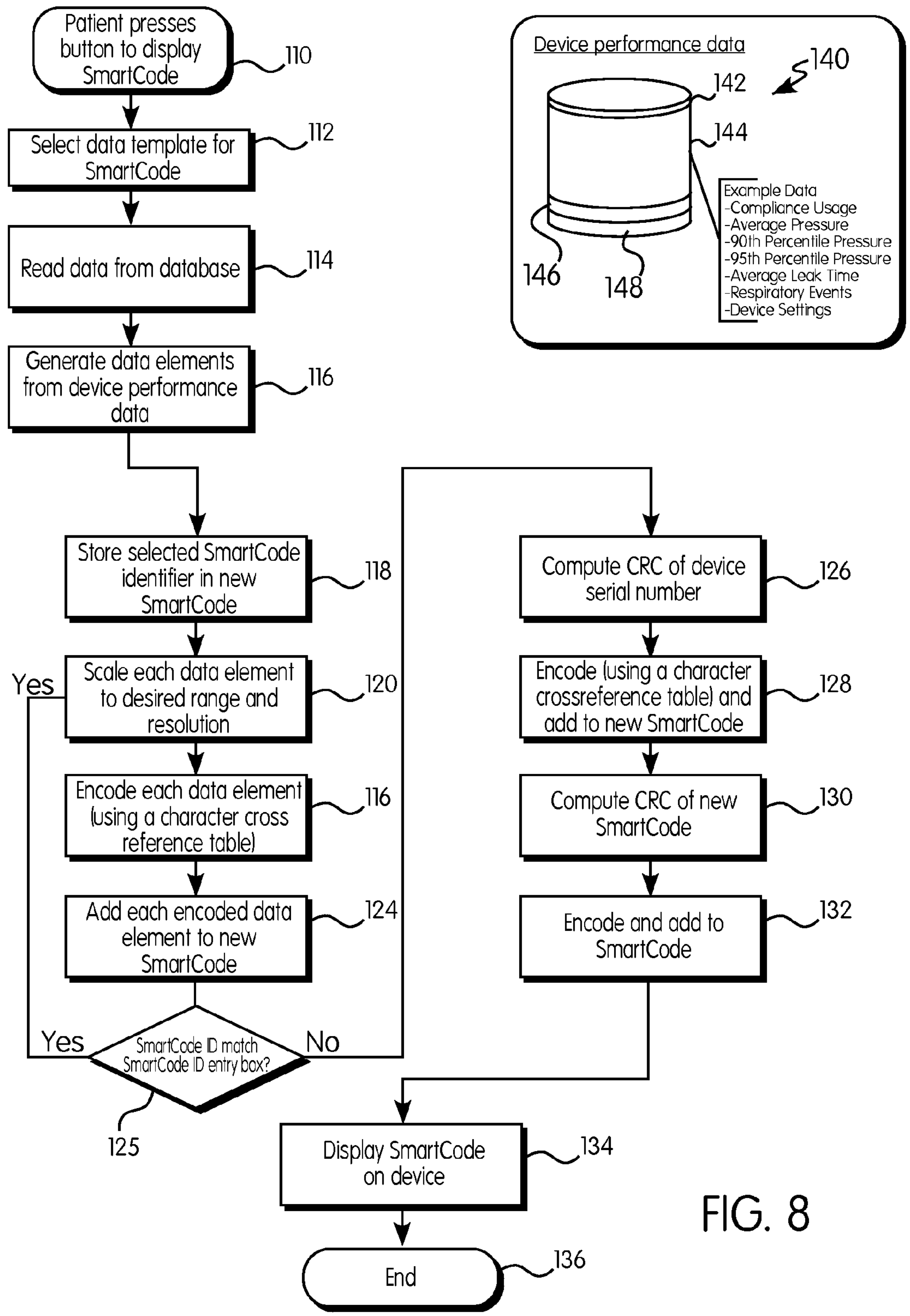
FIG. 8 is a flow chart illustrating process for generating the encoded data strings of the present invention.

The encoded data string is prepared by microprocessor 34 in accordance with encoding algorithm **36*c* stored in non-volatile memory 36. A flow chart illustrating the algorithm is shown in FIG. 8. The algorithm is entered through block 110 when the user presses one of the forward or reverse pushbuttons 52 or 54 or up or down arrow buttons 59 or 58 to select the requested encoded data string. The algorithm advances to functional block 112 where a data template is selected for the currently requested encoded data string. In functional block 114, the data for the selected template is read from the operating parameters and data stored in non-volatile memory 36*d* and the data is manipulated as necessary in functional block 116** to generate the data elements for inclusion in the encoded data string.

During the data manipulation in functional block 116, the desired parameters are computed from the stored operating data. For example, an Exhale Puff Index (EPI) may be calculated from data representing the raw breathing gas pressure and flow that is stored in non-volatile memory 36. Alternately, the desired data may be calculated following each operating session of the breathing gas delivery system and the result stored in the non-volatile memory **36*d*. Additionally, for encoded data strings representing multiple days, such as an encoded data string representing the last 7 days, the average of the daily values is computed in functional block 116**.

Functional blocks 118-124 describe the building of the requested encoded data string. In functional block 118, an identifier corresponding to the requested encoded data string is stored. The identifier is utilized for verification of the encoded data string in decision block 88 of the application shown in FIG. 4. Continuing to functional block 120, one data parameter is scaled to a desired range and resolution. In functional block 122, the data element is encoded using an ASCII character index to a table of values, as described above, with each possible character representing a scaled value of the parameter. Alternatively, other means of data encryption may be used. Next, in functional block 124, the encoded data element is added to the encoded data string. In decision block 125, if there are more parameters to add to the encoded data string, control returns to block 120 and the process is repeated until all desired parameters have been added to the encoded data string.

Continuing to functional block 126, the algorithm computes a CRC for the device-specific identifier. In the preferred embodiment, the device's serial number may be used. The identifier CRC is utilized in optional decision block 92 of the application shown in FIG. 4 for verification of the identifier entered by the provider. The identifier CRC is then encoded and added to the new encoded data string in functional block 128.

The algorithm next proceeds to functional block 130 where a CRC for the new encoded data string as a whole is generated. The CRC for the new encoded data string is utilized in decision block 90 of the application shown in FIG. 4 for verifying that the user read the requested code correctly. The CRC for the encoded data string is encoded and added to the encoded data string in functional block 132.

The encoding in functional block 132 also effectively compresses the data. The new encoded data string is then displayed on display 50 in functional block 134 and the algorithm exits through block 136. If more than one encoded data string is required, the algorithm is re-entered through block 110. It will be appreciated that the components of the encoded data string may be arranged in any desired order than described above.

The invention further contemplates using the described scheme to provide feedback that allows setting adjustments to a specific breathing gas delivery system to be communicated from a remote controlling system to the system (not shown) in an audible format. Such audible formats may include either via DTMF, voice or other protocols suitable with the limitations of audio bandwidth communications equipment. In an alternate embodiment, the device may be supplied with an ASCII keyboard or may provide a connector for connecting a standard computer keyboard to allow the entry of specific codes provided via voice over the telephone. This can be achieved by encoding the setting update command and transmitting it to the therapy device in a manner very similar to the method described above for encoding the operating parameters and data for transmittal to the provider. Multiple protocols may be used, including synthesized voice, DTMF and even a common modem protocol. The breathing gas delivery system would then make setting adjustments. The system would "listen" for correct interface handshaking and commands. The handshaking protocol will preferably include security to ensure communication with the proper breathing gas delivery system, validation to ensure the settings transfer value is not corrupt, and, after the setting adjustments are made, response feedback to ensure the proper setting has been applied to the system.

FIG. 4 is a flow chart representing a process utilized by the provider to request and decode the encoded data string. As previously discussed there is an application into which the provider can enter the codes obtained from the user's device which will decode and verify the encoded data strings and generate reports based on the received data.

Referring to FIG. 4, the provider contacts the user in block 80. In block 82, the provider requests a specific encoded data string, which the user can select by repeatedly pressing arrow buttons 52 and 54 and/or up and down arrow buttons 59 and 58, as required and as previously described. The application then proceeds to decision block 84 where the user reads the encoded data string shown in display 50 repeats it over the telephone connection to the provider. In block 86, the provider enters the encoded data string into a report generator application, an example of which is shown in FIG. 6, via an interface, such as a computer screen and keyboard.

There are two main elements to the provider interface which are combined into the decoder and report generator application; namely, a data input screen and a data output screen. Considering first the data input screen, the screen is displayed upon a computer screen and includes the following data:

- a) Healthcare data input
  - i) Equipment provider information;
  - ii) Physician information;
  - iii) Patient information; and
  - iv) Device information;
- b) Encoded data string entry consisting of places to enter each of the encoded data strings; and.
- c) Validation feedback
  - i) Cyclic Redundancy Check (CRC) code error check
  - ii) Code ID error check
  - iii) Device serial number check The software user, who is typically the healthcare provider, fills out the form shown in FIG. 6 with health care data, then enters the encoded data string received over the telephone from the breathing gas delivery system user. The provider types the encoded data string into the corresponding block on the screen and the application proceeds to apply three checks to the data.

In decision block 88, a code ID error check ensures that the correct code requested by the healthcare provider has been read by the patient. The code ID error check involves counting the number of days above a minimum threshold, the hours of use, or another criteria. Thus, if the healthcare provider requests the 7 Day code but the user mistakenly reads the 30 day code this error will be flagged to the healthcare provider and the second validation box to the right of the corresponding entry box will indicate an error and the application returns to decision block 82 where the provider again requests that the user read the encoded data string. If an error is not detected, the first validation box will turn green and the application transfers to decision block 90.

In decision block 90 in FIG. 4, a CRC code error check helps to ensure that the encoded data string characters have been correctly read by the patient and correctly entered by the healthcare provider. The CRC code error check utilizes a byte that detects errors in the characters as may occur when the user saying the letter "C" over a telephone line is heard by the provider as the letter "E". If an error is detected the first validation box to the right of the corresponding box will indicate, for example, by turning red, that there is an error, and the application returns to functional block 82 where the provider again requests that the user read the same encoded data string. If an error is not detected, the second validation box will provide an indication, for example, by turning green, and the application transfers to decision block 92.

In decision block 92, a breathing gas delivery system serial number check is optionally performed. To select the option, the healthcare provider enters the system serial number in the data input screen. As described above, the CRC calculated based on the serial number information is embedded in each encoded data string and this information is compared to a calculation of the serial number CRC performed based on the serial number entered by the healthcare provider in to the decoding application. If there is a mismatch this error is flagged to the healthcare provider and the third validation box to the right of the corresponding data input box will indicate an error. The application then returns to block 82 where the provider may requests that the user verify the serial number. If an error is not detected, the third validation box will indicate a success status and the application transfers to decision block 94. The application will only continue if none of the validation boxes indicates an error.

In decision block 94, the provider is queried as to whether another encoded data string is desired. If the user wishes to enter another encoded data string, the flow returns to block 82 and the provider requests that the user manipulate buttons 52, 54, 58 or 59 to display the next desired encoded data string. Once all of the desired encoded data strings have been entered, the application proceeds to functional block 96 where the provider may add or change the other information on the screen. The application then continues to functional block 98 where the provider clicks on the "Generate Report" button to decode the entered encoded data strings and generates a report based on the decoded operating parameters and data. The generated report is displayed as a data output screen and includes:

- a) Healthcare data from input screen; and
- b) Decoded data from encoded data strings.

A typical data output screen is illustrated in FIG. 7. The data output screen also may be printed, transmitted to another user and/or stored. The application then exits through block 100.

As described above, the system collects and stores data for one day, seven days, 30 days, 90 days and over a cumulative time period. The data for multiple days and the cumulative time period are averaged for reporting. The one day session encoded data string contains data gathered from the most recent session of breathing device use. The data is fresh so that, while the session data is being compiled, the data is updated in the encoded data string. This allows the user to read the code immediately after waking up without waiting for a time period of non-use of the breathing system to close out the session. As shown in FIG. 5, the encoded data string, in the preferred embodiment, consist of 10 alpha-numeric characters in three groups of three, three and four characters respectively; however, as indicated above, the encoded data string may consist of any number of characters.

In a preferred embodiment of the invention, the first character of the encoded data string represents information about the system identification and the encoded data string to allow the decoding and reporting software to auto-detect the code type. The next eight characters contain operating parameters and data. The tenth character is the serial number CRC character, the detection of which is optional. The final character is the CRC check character that is used to validate the encoded data string.

Note that any one of a number of well known polynomials may be used to generate the CRC code, but, in the preferred embodiment, a CRC-8 polynomial of the form $x^8+X^5+X^4+1$ is used.

The invention also contemplates utilization of alternate means of data transmission to the provider. Thus, the invention contemplates that the data can be transmitted by means other than a patient reading an encoded data string over a telephone link. Such methods of transmitting the data may be user-initiated, device-initiated or provider-initiated. To utilize such methods, the device may be provided with a telephone line connection, satellite connection or internet connection, or may utilize separate devices which may be connected via a data link to the device, such as a modem. These methods may include, but are not limited to:

(a) Encoding and transmitting in an audible format such as, for example, DTMF (Dual Tone Multiple Frequency);

(b) Frequency or similar method wherein the device would "play" the encoded information to a phone receiver;

(c) Synthesized voice or other protocol suitable with the limitations of audio bandwidth communications equipment wherein the device would "speak" the encoded information to a telephone receiver; and (d) emails, SMS messages, or any other method known in the art for communicating ASCII strings.

The system may also include a feedback modulation schema for tone or DTMF signaling. When an audible link is present in a communication scheme it increases the likelihood of artifacts and interference. It is a significant challenge to maintain enough of a signal-to-noise ratio for a receiver to discriminate the information from background noise. The signal can easily be too small to detect or too loud causing distortion. Several modulation techniques may be utilized to improve the likelihood of a successful transmission, namely:

(a) Modulate each tone (ramp minimum to maximum) individually, wherein each tone's amplitude is ramped in amplitude from a low level to a high level. As the tone increases to sufficient amplitude above the background the receiver will detect it and as the amplitude continues to increase it may reach the maximum level possibly causing distortion however it would have already been detected successfully. This allows a single tone burst to be transmitted successfully across systems with diverse audio links.

(b) Modulate each sequence as a whole wherein each sequence of tones is transmitted starting with a lower level and repeating with the entire sequence with higher and higher amplitude until a successful receipt is acknowledged.

(c) Modulate a "test" sequence from low level to high level until it is detected successfully, Then increase the amplitude to provide some additional margin and use this level for transmitting the code.

The device may also include a session detection feature that requires that the breathing device be powered while in an OFF state and includes the following stages:

(1) Start Session—Detection after a predetermined time period of continuous use (for example, a half hour);

(2) Trip hour meter counts while user is breathing from beginning of half hour period; and (3) Stop Session—Detection of a predetermine time period of non-used (for example, four hours).

The system also adds any time for a napping period within 24 hours of the stop session to the trip hour meter.

In an alternate embodiment of the breathing gas delivery system control unit a monitoring module may be attached to the rear of the control unit by a technician into which a removable memory card may be inserted. The monitoring module is operative to record the selected operating data described above. However, instead of requiring that the device user transmit the encoded data to the provider, the technician periodically visits the user and collects the memory card, or the user sends the memory card to the provider and is supplied with a replacement. Alternately, the user may use an application on a local computer to read the card and transmit the data to the provider. Thus, the user need not be involved in the process of data collection. After removing the memory card, the technician may either insert a new memory card for further data collection or, if the monitoring is complete, remove the monitoring module. Upon returning to the clinic or physician's office, the technician would download the contents of the memory card into a computer and then log onto the report generating service or application to decode the data and generate a report as described above.

The invention and primary modes of operation have been explained and illustrated in its preferred embodiment. However, it must be understood that this invention may be practiced otherwise than as specifically explained and illustrated without departing from its spirit or scope. As such, the invention also contemplates that other, or additional, features, such as alternate operating parameters may be monitored and provided as output data. For example, a humidity sensor (not shown) may be added to the device to provide for monitoring and storage of data regarding the humidity of the breathing gas delivered by the system. Also, as previously stated, the invention is not limited to use with CPAP or breathing gas delivery systems, but may be utilized with other medically-related or non-medical devices.

What is claimed is:

1. A breathing therapy device comprising:

a. a blower, for delivering pressurized air to a user of said device;

b. a processor, for controlling said blower;

c. non-volatile memory, accessible by said processor, said non-volatile memory containing an area for storage of operating parameters and usage data;

d. an algorithm, stored in said non-volatile memory, for encoding usage data regarding the duration of the use of said device over a specified time period into one or more strings of readable characters such that the true values of said usage data is obfuscated from the user of said device; and e. a display element, for displaying said one or more strings of readable characters.

2. The breathing therapy device of claim 1 wherein said usage data includes information necessary to determine the usage of said device.

3. The breathing therapy device of claim 1 wherein said usage data includes information regarding the number of sleep apnea, sleep hypopnea, or other sleep related events experienced by the user during the usage of said device.

4. The breathing therapy device of claim 1 wherein said usage data includes usage data collected over pre-determined periods of time.

5. The breathing therapy device of claim 4 wherein said usage data is averaged over a pre-determined period of time prior to being encoded.

6. The breathing therapy device of claim 5 wherein said pre-determined period of time are selected from a group consisting of the last 7 days, the last 30 days and the last 90 days.

7. The breathing therapy device of claim 1 wherein at least one of said strings of readable characters includes one or more characters regarding the type and identity of said breathing therapy device.

8. The breathing therapy device of claim 1 where said one or more strings each contain one or more characters identifying the type of data included in said string.

9. The breathing therapy device of claim 1 further comprising a control element which allows the user to control which string of readable characters is displayed.

10. The breathing therapy device of claim 1 wherein each of said strings of readable characters includes one or more error checking characters.

11. The breathing therapy device of claim 1 wherein each character in said one or more strings of readable characters which represent encoded data serves as an index to a table containing actual values for the data or ranges of values for the data.

12. The breathing therapy device of claim 11 wherein said usage data is scaled such as to fit within said ranges of values in said table.

13. The device of claim 1 further comprising an input element which allows the user of the device to enter encoded strings of readable characters, said encoded strings of readable characters containing new operating parameters for said device.

14. A method of retrieving usage data from a breathing therapy device comprising the steps of:

instructing a user of said device to manipulate said device such as to cause said device to display one or more strings of readable characters, said strings of readable characters representing data regarding the use of said device by the user, said data being encoded such as to obfuscate the actual value of said data from the user;

receiving from said user said one or more strings of readable characters; and decoding said one or more strings of readable characters to retrieve said usage data.

15. The method of claim 14 wherein said usage data includes information regarding the number of sleep apnea, sleep hypopnea, or other sleep related events experienced by the user during the usage of said device.

16. The method of claim 14 wherein said usage data includes averages of usage data collected over pre-determined periods of time.

17. The method of claim 14 wherein at least one of said strings of readable characters includes one or more characters regarding the type and identity of said breathing therapy device.

18. The method of claim 14 wherein each character in said one or more strings of readable characters which represent encoded data serves as an index to a table containing actual values for the data or ranges of values for the data.

19. A method of remotely programming a breathing therapy device, comprising the steps of:

communicating one or more strings of readable characters to a user of the device, said strings of readable characters representing operating parameters which have been encoded such as to obfuscate the actual value of said operating parameters from the user; and instructing the user to manipulate said breathing therapy device to input said one or more strings of readable characters to said device.

20. The method of claim 19 wherein said encoded parameters include pressure level settings indicating therapy pressures for said user.

21. The method of claim 19 wherein said breathing therapy device displays an encoded verification string that can be used to confirm that the inputted string was properly received and executed by the device.

* * * * *